(12) United States Patent
Bales

(10) Patent No.: US 7,985,791 B1
(45) Date of Patent: Jul. 26, 2011

(54) INCORPORATION OF SBP AND ULEXITE INTO COMPOSITES

(75) Inventor: Stephen G Bales, Sewell, NJ (US)

(73) Assignee: Lords Additives LLC, Sewell, NJ (US)

( * ) Notice: Subject to any disclaimer, the term of this patent is extended or adjusted under 35 U.S.C. 154(b) by 198 days.

(21) Appl. No.: 12/378,691

(22) Filed: Feb. 17, 2009

Related U.S. Application Data

(60) Provisional application No. 61/066,496, filed on Feb. 22, 2008.

(51) Int. Cl.
  *C08K 3/38* (2006.01)
  *B29C 47/00* (2006.01)
  *C09D 5/16* (2006.01)
  *C09D 5/18* (2006.01)
(52) U.S. Cl. .......... 524/405; 524/13; 106/18.13
(58) Field of Classification Search .......... 524/13, 524/405; 106/18, 18.3
  See application file for complete search history.

(56) References Cited

U.S. PATENT DOCUMENTS

| | | | | |
|---|---|---|---|---|
| 2,940,942 | A * | 6/1960 | Hodenfield | 252/607 |
| 3,135,648 | A * | 6/1964 | Hawkins | 428/511 |
| 3,865,760 | A * | 2/1975 | Pitts et al. | 521/85 |
| 3,897,387 | A * | 7/1975 | O'Shaughnessy | 524/281 |
| 3,945,962 | A * | 3/1976 | Clark | 524/99 |
| 4,039,645 | A * | 8/1977 | Coyle | 264/118 |
| 4,076,580 | A * | 2/1978 | Panusch et al. | 162/159 |
| 4,113,652 | A | 9/1978 | Yoshikawa et al. | |
| 4,144,288 | A * | 3/1979 | Miano | 524/112 |
| 4,144,304 | A * | 3/1979 | Dereppe et al. | 264/175 |
| 4,400,298 | A * | 8/1983 | Boocock et al. | 252/400.4 |
| 4,595,414 | A * | 6/1986 | Shutt | 106/18.16 |
| 4,719,110 | A * | 1/1988 | Patel et al. | 424/660 |
| 4,879,083 | A | 11/1989 | Knudson et al. | |
| 4,935,457 | A | 6/1990 | Metzner et al. | |
| 5,075,360 | A * | 12/1991 | Fitt et al. | 524/48 |
| 5,246,652 | A | 9/1993 | Hsu et al. | |
| 5,516,472 | A | 5/1996 | Laver | |
| 5,648,415 | A * | 7/1997 | Hoeks et al. | 524/405 |
| 5,684,117 | A * | 11/1997 | Londa et al. | 528/220 |
| 5,763,338 | A | 6/1998 | Sean | |
| 5,855,817 | A * | 1/1999 | Walker | 252/400.41 |
| 6,030,562 | A * | 2/2000 | Lehtinen et al. | 264/83 |
| 6,270,883 | B1 | 8/2001 | Sears et al. | |
| 6,410,632 | B1 * | 6/2002 | West | 524/405 |
| 6,440,908 | B2 * | 8/2002 | Racherla | 510/122 |
| 7,001,942 | B2 * | 2/2006 | Rogers et al. | 524/414 |
| 7,666,254 | B1 * | 2/2010 | Romero et al. | 106/18.3 |
| 2003/0030042 | A1 * | 2/2003 | Sawada et al. | 252/604 |
| 2006/0172987 | A1 | 8/2006 | Groenendaal et al. | |
| 2007/0001337 | A1 * | 1/2007 | Bales | 264/122 |
| 2007/0149722 | A1 * | 6/2007 | Fujiguchi et al. | 525/464 |
| 2007/0190876 | A1 * | 8/2007 | Ogawa et al. | 442/136 |
| 2008/0090480 | A1 * | 4/2008 | Akimoto et al. | 442/328 |
| 2008/0303006 | A1 * | 12/2008 | Huijs et al. | 252/609 |
| 2010/0062166 | A1 * | 3/2010 | Betts | 427/384 |

FOREIGN PATENT DOCUMENTS

EP 1612020 A2 * 1/2006

OTHER PUBLICATIONS

Ulexite, Encylcopedia Britannica Online, 2010.*
Steven Verhey, Peter Laks, Bana Richter, "Laboratory Decay Resistance of Woodfiber/Thermoplastic Composites", Forest Products Journal, vol. 51, Sep. 2001.
Demirkiran: Brazilian Journal of Chemical Engineering "Dissolution kinetics of ulexite prepared under different calcination temperatures" Introduction para Dec. 3, 2008, p. 1-2.

* cited by examiner

*Primary Examiner* — Mark Eashoo
*Assistant Examiner* — Liam J Heincer

(57) ABSTRACT

Sodium tetraborate pentahydrate (SBP) and Ulexite, which release their waters of hydration at 120° C. and 59° C. respectively, can be modified to allow their use as fungicides in lignocellulosic, lignocellulosic thermoplastic, and thermoplastic composites even though processing temperatures for those composites range from about 150° C. to over 300° C. This is accomplished by modifying two boron-containing chemicals prior to their incorporation into the composites. The modification involves the heating of the two chemicals followed by the mixing of the results with glycerol mono stearate (GMS). In other embodiments only heating or mixing with GMS is utilized.

20 Claims, No Drawings ated paper filed Feb. 22, 2008

INCORPORATION OF SBP AND ULEXITE INTO COMPOSITES

CROSS-REFERENCE TO RELATED APPLICATIONS

61/066,496 filed Feb. 22, 2008

FEDERALLY SPONSORED RESEARCH

None

SEQUENCE LISTING

None

BACKGROUND

This invention relates to the incorporation of sodium tetraborate pentahydrate (SBP) and naturally occurring calcium sodium borate (Ulexite), which begin to release waters of hydration at 120° C. and 59° C. respectively, into lignocellulosic, lignocellulosic thermoplastic, and thermoplastic composites that require processing temperatures from about 150° C. to 300° C. Specifically it describes a processes that modifies SBP and Ulexite prior to their incorporation into the final composite product by heating to eliminate a portion of their waters of hydration followed by mixing the resultant product with glycerol mono stearate (GMS). In alternative embodiments of the invention the heating step or the mixing step of the process is deleted.

There is a very high demand for wood products. Although wood is a renewable resource, it takes many years for trees to mature. Consequently, the supply of wood suitable for use in construction is decreasing and there is a need to develop alternative materials. One alternative has been the use of lignocellulosic composites in applications which require resistance to wood-destroying organisms such as fungi and insects. This requires treatment of these composites with a wood preserving material.

Traditionally solid wood products are dipped or pressure treated with solutions of fungicides to provide resistance to fungus and mould damage. However with a composite material, the fungicide can be incorporated during its production. This approach yields a product in which the lignocellulosic composite has a constant loading of preservative throughout its thickness, strengthening its resistance to leaching and increasing the effectiveness of the preservative.

Lignocellulosic composites are formed with thermosetting resins which undergo a chemical reaction when heated causing the resin to harden. Lignocellulosic based composites include particleboard, oriented strand board (OSB), fiberboard (medium and high density), laminated strand lumber and similar products. The methods for manufacturing thermosetting lignocellulosic composites are generally well known but the specific procedure will depend on the cellulosic material and the type of composite desired. However, generally the lignocellulosic material is processed into fractions or particles of appropriate size, which may be called a furnish, mixed with an adhesive thermosetting resin and the resultant mixture is formed into the desired configuration such as a mat, and then formed, usually under heat and pressure into the final product. The process is usually a dry one; that is generally no water is added to form a slurry of the materials; however a water slurry may be used in some processes. The resin can be of a phenol formaldehyde (PF) or iso-cyanate type and can be from about 2 to as much as 25 percent by weight of the total composite.

Many attempts have been made to use three types of hydrated sodium borates (SBP), sodium tetraborate decahydrate (SBD), and disodium octaborate tetrahydrate (DOT)) in composite products as these chemicals are low in cost and mammalian toxicity and have a minimum environmental impact. However, when phenol formaldehyde resins are used as a binder, these three borates either reduce the adhesive bonding to unacceptable levels at very low boron retentions or they require special processing techniques. Knudson et al in U.S. Pat. No. 4,879,083 issued Nov. 17, 1989 recognized that the strength of waferboard was reduced to an unacceptable level when disodium octaborate tetrahydrate was used as an additive. Hsu et al in U.S. Pat. No. 5,246,652 teaches that the use of DOT or SBP requires the use of a resin that does not react readily with these borates. Hsu identifies a requirement for as a "two-stage" (novolac) phenol formaldehyde (PF) resin as opposed to the typical "one-stage" (resole) PF used in OSB production. He also states that if a resole PF resin is used the final composite must be formed using pressurized steam preferably in a self-sealing or sealed steam press.

Knudson teaches that when anhydrous borax (sodium tetraborate with no waters of hydration) can be used as an additive and preserve the bond strength. However the production of anhydrous borax starts with the decahydrate or pentahydrate forms and requires a significant amount of energy and associated cost to totally dehydrate the chemical. Neither Hsu or Knudson discuss the use of SBP when incorporated into a lignocellulosic composite that utilizes an isocyanate-based resins.

Thermoplastic lignocellulosic composites are formed with thermoplastic resins that do not react chemically when heated. The processing methods are quite different from those associated with lignocellulosic composites. Although some of these methods are well known, others are continually being developed as this composite type continues to occupy a larger share of the construction marketplace. Lignocellulosic materials such as wood, sawdust, rice hulls, and the like are added to thermoplastic compounds to achieve a wood-like composite providing reinforcement, reduced coefficient of expansion, and cost reduction. Process methods have been developed to enable blends containing materials having low bulk density (ie. powders) and poor flow characteristics to be fed at commercially acceptable rates. Blends of this type can be extruded through dies of the appropriate configuration to produce building product type shapes previously made from wood. Processing temperatures using these methods range usually range from approximately 150 to 200° C., although some processes operate at temperatures above approximately 300° C.

When lignocellulosic thermoplastic composites were first introduced, the prevailing theory was that the plastic protected the cellulose from fungal attack. However research has revealed that lignocellulosic thermoplastics are susceptible to structural damage from fungal decay and cosmetic surface impairment from mold. See Verhey, Laks, and Richer, "Laboratory Decay Resistance of Woodfiber/Thermoplastic Composites", Forest Products Journal, September 2001, Vol. 51 p 44-50. Further, since the primary use of lignocellulosic thermoplastics is in decking and railing products which are exposed to the elements, surface degradation due to weathering is an issue. Weathering is a complex process which includes ultraviolet (UV) light interaction and aging of the materials due to exposures such as acid rain.

Degradation due to the fungal attack is a problem that threatens the material's structural integrity. Surface lightening, discoloration, and spotting caused by mold spore production and weathering is a problem since major commercial uses of lignocellulosic thermoplastic composites, including decking and railing, rely on their aesthetic appeal to compete in the marketplace.

Zinc Borate has been used successfully to provide fungal decay in lignocellulosic thermoplastic composites at relatively low levels, typically less than 1.5 percent. However zinc borate is an expensive material when compared to the cost of the plastic binder, and its addition increases the composite's total cost. SBP and Ulexite have temperature limitations that prevent their use in many of the thermoplastic processes as they start to lose their waters of hydration at approximately 120° C. and 59° C. respectively which can cause processing problems such as excessive heat buildup during mixing or extrusion. A release of moisture can cause equipment damage via overheating or require a slow down in product output to compensate for potential overheating.

Currently the lignocellousic thermoplastic composites industry is faced with two preservation needs: finding an economic method of improving resistance to fungal decay and developing a method for improving resistance to surface visual impairment caused by mold and weathering.

Thermoplastic composites which are processed at temperatures usually in excess of 160° C., and can exceed 300° C., contain no lignocellulosic material and therefore are not vulnerable to fungal decay and insect attack. However they are susceptible to surface impairment caused by mold, especially when the material is located in a dark, moist environment as well as impairment caused by weathering. The addition of the modified SBP and Ulexite described in this invention allows their incorporation at the processing temperatures encountered when manufacturing these composites. This incorporation provides a resistance to the surface impairment.

Removing a portion of the waters of hydration in SBP and Ulexite also produces other benefits. A lesser amount by weight of the chemical is required to produce a similar level of resistance to mold or fungal decay in the composite; this is beneficial as often additional material in a composite can reduce desirable properties such as bond strength. Further, eliminating additional weight from SBP and Ulexite reduces their transportation costs.

SUMMARY AND OBJECTIVES OF THE INVENTION

SBP and Ulexite are low cost, environmentally friendly boron containing fungicides but give off their waters of hydration at temperatures lower than those required in the manufacturing of composites. This release of water inside the composite compounding equipment can require a reduction in production throughput, or can prevent the use of these two chemicals. The present invention describes a processes that address the above outlined needs by modifying SBP and Ulexite to permit their incorporation into the three types of composite materials.

The first step in the process is the heating of SBP ($Na_2B_4O_7.5H_2O$) to produce sodium tetraborate trihydrate ($Na_2B_4O_7.3H_2O$) and sodium tetraborate dihydrate ($Na_2B_4O_7.2H_2O$), called SB 3 mol and SB 2 mol (or simply 3 mol and 2 mol) respectively. These two sodium tetraborate hydrates, which can be produced by subjecting them to significantly less heating then that required to produce anhydrous borax, can sustain processing temperatures required to make lignocellulosic thermoplastic and thermoplastic composites without additional release of hydration waters.

Similar heating of Ulexite ($Na_2O.2CaO.5B_2O_3.16H_2O$) reduces the percentage of waters of hydration from 35 percent to approximately 6 percent. This provides benefits comparable to those from 2 and 3 mol sodium tetraborate. For purposes of this invention, this modified product will be called modified Ulexite.

The second step is the mixing of 2 mol, 3 mol, or modified Ulexite with glycerol mono stearate (GMS) in a ratio of from about 3:1 to 200:1 which allows the resultant mixture to be used in compounding processes at temperatures as high as approximately 300° C. This mixture will be referred to in this invention as Modified Borate/GMS. The addition of GMS adds approximately 50 to 60° C. to the temperature where the waters of hydration start to be released.

In an embodiment of this invention, mixing with GMS is eliminated and the 2 mol, 3 mol, and modified Ulexite are used directly in composite products under certain conditions. Since they contain a lower percentage of waters of hydration these chemicals can be incorporated without GMS into lignocellulosic composites with less impact on the resulting bond strength. As a result they do not require the "two stage" (novolac) PF resins or the special steam press measures identified by Hsu for SBP and DOT. And all three can be used without GMS in lignocellulosic thermoplastic and thermoplastic composites where processing temperatures are less than about 200° C. For those manufacturing processes requiring temperatures above 200° C. but below about 300° C. the 2 mol without GMS can be utilized.

In another embodiment of this invention, the combination of SBP with GMS, which for this invention is called SBP/GMS, can be used in lignocellulosic thermoplastic or thermoplastic composites whose processing temperatures are less than about 170° C.

DETAILED DESCRIPTION

The lignocellulosic thermoplastic composites of this invention are produced by procedures that combine molten plastic with lignocellulosic fiber and additional additives such as lubricants, process aids, cross-linking agents, inhibitors, stabilizers, blowing agents, foaming agents and other additives. Examples of suitable thermoplastics include polyethylene (PE), high density polyethylene (HDPE), polystyrene (PS), and polyvinyl chloride (PVC) with loadings by weight from 20% to 75%. The lignocellulosic component of these composites can range from about 20% to 75% by weight. This process is further described in U.S. Pat. No. 5,516,472 (May, 1996). U.S. Pat. No. 6,270,883 describes the use of polyamides (nylon), PET (polyethylene terephthalate), PBT (polybutylene terephthalate), PIT (polytrimethylene terephthalate), SAN (styrene/acrylonitrile), SMA (styrene/maleic anhydride), or mixtures thereof as thermoplastic resins. Examples of suitable lignocellulosic material include wood, ground rice hulls, kenaf, jute, bamboo, and coconut shells.

The methods for manufacturing lignocellulosic filled thermoplastic depend on the cellulosic raw material, the plastic, and the type of cellulosic thermoplastic composite desired. However, in general the raw materials are mixed together in a compounding process and the compounded material is then formed into the desired product.

Alternatively, the 2 mol, 3 mol, or modified Ulexite can be compounded in a highly loaded pellet containing at least 50 percent of the chemical with the remainder a thermoplastic such as low linear density polyethylene. In this latter case, the melt index of this pellet should be greater that 1 to allow its incorporation into the final lignocellulosic thermoplastic product. Melt index is the number of grams of plastic that can be pushed out of a capillary die under a standard weight in 10 minutes.

Compounding of the lignocellulosic thermoplastic composite is performed by the feeding and dispersing of the lignocellulosic material, fillers and additives, including the 2 mol/GMS, 2 mol, 3 mol/GMS, 3 mol, modified Ulexite/GMS, Modified Ulexite or SBP/GMS into the molten polymer using either batch or continuous mixers. Temperatures during the compounding process normally range from 150° C. to above 300° C. SBP/GMS can be used for processing temperatures up to about 170° C., 3 mol and modified Ulexite for temperatures up to about 200° C., 3 mol/GMS and modified Ulexite/GMS for temperatures up to about 250° C., 2 mol for temperatures up to about 300° C., and 2 mol/GMS for temperatures up to about 350° C. The compounded material then is either immediately pressed into the end product or formed into intermediate pellets for future processing.

Thermoplastic composites are processed in a similar manner without the addition of lignocellulosic material. Processing temperatures can also be as high as 300° C.

The exact particle size of particulate 2 mol, 3 mol, SBP/GMS, modified Ulexite and Modified Borate/GMS is not critical, but the material must be of a size that can be dispersed uniformly throughout the lignocellulosic or lignocellulosic-thermoplastic composite. Generally a mean particle size as large as 150 microns and as small as 1 micron can be used.

The 2 and 3 mol versions are produced by heating SBP (5 mol) to release its waters of hydration. Control of the specific hydrate form is accomplished by specific temperature and time conditions. Because two of the water molecules in 5 mol exist as hydroxyl groups, their removal requires significant amounts of energy. This requires temperatures in excess of 1000° C. However elimination of the other 3 molecules is accomplished via dehydration at relatively lower temperatures with lower cost. Although a number of time and temperature profiles will produce 2 or 3 mol versions, the following are illustrative. The 3 mol version can be produced from SBP (5 mol) by maintaining a temperature of between 124-128° C. for 30-40 minutes while an additional period of 15 minutes at 150-160° C. makes 2 mol. As a result the 3 mol material without GMS added is able to withstand approximately 200° C. composite processing temperatures since the duration at this temperature during the processing of the final composite product is relatively short. Similarly the 2 mol material without GMS can withstand composite processing temperatures up to about 300° C.

Ulexite starts to give off its waters of hydration at 59° C. and heating to approximately 200° C. produces modified Ulexite which without GMS can sustain the processing temperature of approximately 200° C. before releasing further waters of hydration.

In this invention the term SBP/GMS is defined as 5 mol mixed with glycerol mono stearate (GMS) in a ratio from about 3:1 to 200:1. This modification allows 5 mol to delay the initial release of its waters of hydration from about 120° C. until approximately 170° C. As a result SBP/GMS can be used in lignocellulosic thermoplastic composite processes that operate below about 170° C.

Mixing 2 mol, 3 mol, and modified Ulexite with GMS in a ratio of from about 3:1 to 200:1 increases the maximum processing temperature each of these three chemicals can withstand by about 50° C.

The amount of 2 mol, 3 mol, SBP/GMS, or modified Ulexite incorporated into the composite material will depend on the longevity desired and the anticipated exposure to moisture. In general, when resistance to decay caused by fungus is required, a range of about 0.1 to 3 percent by weight of the chemical is required. Preferable an amount from 0.5 to 2 percent is required.

When increased resistance to visual surface impairment caused by mold or weathering is required, the amount will be in the range of about 1 to 12 percent. Preferable an amount from about 3 to 5 percent is required.

What is claimed is:

1. A method of producing a lignocellulosic thermoplastic or thermoplastic composite product that has been treated with a boron containing compound comprising heating of sodium tetraborate pentahydrate (SBP) or ulexite to form sodium tetraborate trihydrate, sodium tetraborate dihydrate or modified ulexite mixing of the sodium tetraborate trihydrate, sodium tetraborate dihydrate, or modified ulexite with glycerol mono stearate (GMS) in a ratio from about 3:1 by weight to 200:1 by weight, and incorporating at least one of these boron compound and GMS mixtures in a range of from about 1 to about 10 percent by weight of the total composite into the ingredients of the composite either before or during processing.

2. The method according to claim 1 in which said amount of boron-containing compound is in a range of from about 3 to about 5 percent.

3. The method according to claim 1 in which said boron containing compound is sodium tetraborate dihydrate or sodium tetraborate dihydrate.

4. The method according to claim 1 in which said lignocellulosic material is wood.

5. The method according to claim 1 in which said thermoplastic material is selected from the group consisting of polyethylene, high-density polyethylene, polystyrene, and polyvinyl chloride.

6. The method according to claim 1 in which said thermoplastic material is selected from the group consisting of polyamides, PET (polyethylene terephthalate), PBT (polybutylene terephthalate), PTT (polytrimethylene terephthalate), SAN (styrene/acrylonitrile), SMA (styrene/maleic anhydride), or mixtures thereof.

7. A method of producing a thermoplastic composite product that has been treated with a boron containing compound comprising heating of sodium tetraborate pentahydrate (SBP) or ulexite to form sodium tetraborate trihydrate, sodium tetraborate dihydrate or modified ulexite and incorporating at least one of these boron containing compounds in a range of from about 50 to 80 percent by weight of the total composite into the ingredients of the composite either before or during processing.

8. The method according to claim 7 where said thermoplastic material is polyethylene, low density polyethylene, or low linear density polyethylene.

9. The method according to claim 7 where said boron containing compound is sodium tetraborate trihydrate or sodium tetraborate dihydrate.

10. A method of producing a lignocellulosic or lignocellulosic thermoplastic composite product that has been treated with a boron-containing compound comprising heating of sodium tetraborate pentahydrate (SBP) or ulexite to form sodium tetraborate trihydrate, sodium tetraborate dihydrate or modified ulexite, then incorporating at least one of these boron containing compounds in a range of from about 0.1 to 3 percent by weight of the total composite into the ingredients of the composite either before or during processing.

11. The method according to claim 10 in which the amount of said boron-containing compound is in the range of from about 0.5 to 2 percent.

12. The method according to claim 10 in which said lignocellulosic composite employs an iso-cyanate resin.

13. The method according to claim 10 in which said lignocellulosic composite employs a phenol formaldehyde adhesive.

14. The method according to claim 10 in which said lignocellulosic composite employs a phenol-resorcinol formaldehyde adhesive.

15. The method according to claim 10 in which said lignocellulosic material is wood.

16. The method according to claim 10 in which said thermoplastic material is selected from the group consisting of polyethylene, high-density polyethylene, polystyrene, and polyvinyl chloride.

17. The method according to claim 10 in which said boron containing compound is sodium tetraborate trihydrate or sodium tetraborate dihydrate.

18. A method of producing a thermoplastic composite product not containing lignocellulosic material that has been treated with a boron-containing compound comprising the mixing of sodium tetraborate pentahydrate (SBP) with glycerol mono stearate (GMS) in a ratio from about 3:1 by weight to 200:1 by weight and incorporating the SBP/GMS mixture in the range of from about 1 to about 12 percent by weight of the total composite into the ingredients of the composite either before or during processing.

19. The method according to claim 18 in which said boron containing compound is in the range of from about 3 to about 5 percent.

20. The method according to claim 18 in which said thermoplastic material is selected from the group consisting of polyethylene, high-density polyethylene, polystyrene, and polyvinyl chloride.

\* \* \* \* \*